United States Patent [19]

Kondo et al.

[11] Patent Number: 5,290,477
[45] Date of Patent: Mar. 1, 1994

[54] OPTICALLY ACTIVE COMPOUND AND LIQUID CRYSTAL COMPOSITION CONTAINING THE SAME

[75] Inventors: Hitoshi Kondo; Mika Tadokoro; Hiroshi Sugiyama; Toshimitsu Hagiwara; Takashi Imai; Mamoru Yamada; Keisuke Itakura, all of Kanagawa, Japan

[73] Assignee: Takasago International Corporation, Tokyo, Japan

[21] Appl. No.: 98,937

[22] Filed: Jul. 29, 1993

[30] Foreign Application Priority Data

Jul. 30, 1992 [JP] Japan .................................. 4-222296
Jun. 1, 1993 [JP] Japan .................................. 5-152583

[51] Int. Cl.⁵ ...................... C09K 19/34; C09K 19/52; C07C 43/02; C07D 239/02
[52] U.S. Cl. .................. 252/299.61; 252/299.01; 544/242; 544/298; 544/318; 544/335; 568/588; 568/631; 568/647
[58] Field of Search ...................... 252/299.01, 299.61; 544/242, 298, 318, 335; 568/588, 631, 647

[56] References Cited

FOREIGN PATENT DOCUMENTS 4-29954 1/1992 Japan .

Primary Examiner—Shean Wu
Attorney, Agent, or Firm—Sughrue, Mion, Zinn, Macpeak & Seas

[57] ABSTRACT

An optically active compound represented by formula (I):

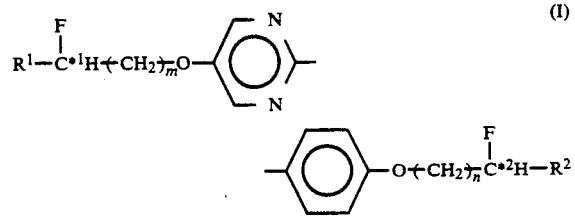

wherein $R^1$ represents an alkyl group having from 3 to 9 carbon atoms; $R^2$ represents an alkyl group having from 3 to 7 carbon atoms; m and n each represent 1 or 2 provided that they do not simultaneously represent 1; and $C^{*1}$ and $C^{*2}$, both represent an optically active carbon atom, and a liquid crystal composition containing the same are disclosed. The compound exhibits chiral nematic and smectic phases and are excellent as a chiral dopant for ferroelectric liquid crystal compositions or nematic liquid crystal compositions.

2 Claims, No Drawings

OPTICALLY ACTIVE COMPOUND AND LIQUID CRYSTAL COMPOSITION CONTAINING THE SAME

FILED OF THE INVENTION

This invention relates to a novel optically active compound, and particularly a compound showing a chiral smectic liquid-crystal phase, and a liquid crystal composition containing the same as an optically active additive. It also relates to a liquid crystal composition applicable to electro-optic elements.

BACKGROUND OF THE INVENTION

Liquid crystal displays have been used in various embodiments such as watches and electronic calculators because of their thinness, lightness, and low power driving properties. With the advancement of integrated circuits (IC), liquid crystal displays have been increasing the display size and extending their use in computers, liquid crystal TV sets, etc. in place of conventional cathode-ray tubes.

However, nematic liquid crystals which have conventionally been used have a slow response as needing a switching time of from 10 to 50 milliseconds and also undergo a reduction in display contrast with increases in number of pixels and in display area.

In the state-of-the-art liquid crystal displays, the above-described disadvantages are coped with by providing a thin film transistor (TFT) on each pixel to achieve so-called active matrix driving or by increasing the angle of twist of liquid crystal molecules sandwiched between a pair of substrates to 220° to 270° (called super-twisted nematic mode: STN).

Mounting of TFT according to the former means not only entails very high cost but has a poor yield, resulting in an increased production cost. Cost reduction by introducing a large-scaled production line having been studied, there is a limit due to essential involvement of many production steps. Further, ever since the appearance of high-definition televisions (HDTV), there has been an increasing demand of liquid crystal displays making a high-density display. In nature of TFT and nematic liquid crystals, it is nevertheless considered very difficult to increase display density.

Although the STN mode exhibits an increased contrast ratio, it has a longer response time as long as 100 to 200 milliseconds and is thus limited in its application.

On the other hand, ferroelectric liquid crystals which were proposed by N. A. Clark, et al. as surface-stabilized ferroelectric liquid crystal devices (SSFLD) (refer to N.A. Clark, et al., *Appl. Phys. Lett.*, Vol. 36, p. 899 (1980) have been attracting attention for their fast response reaching about a thousand times that of nematic liquid crystals.

However, such a fast response time is a result obtained in a high temperature range, and the response time obtained around room temperature is impractically as long as several tens of microseconds. Besides, there remains an unsolved problem in molecular orientation. Therefore, ferroelectric liquid crystal display elements have not yet been put to practical use. In particular, the molecular orientation of ferroelectric liquid crystals proved more complicated than thought by Clark, et al. That is, the director of liquid crystal molecules is apt to be twisted in a layer, with which a high contrast ratio cannot be achieved. Further, the layers have been believed to be aligned upright and perpendicular to the upper and lower substrates (bookshelf structure) but, in fact, were found to have a bent structure (chevron structure). As a result, zigzag defects develop to reduce a contrast ratio.

It is known that a response time of ferroelectric liquid crystals is dependent on spontaneous polarization, which develops depending on the dipole moment in the direction perpendicular to the long axis of the molecule, chirality and the orientation of the dipole, rotational viscosity, and intensity of the applied electric field. However, there is a limit of voltage which can be practically derived from an IC used in combination, and a compound having a low viscosity and exhibiting high spontaneous polarization has not been discovered. From these and other reasons, the response time of ferroelectric liquid crystals has not yet been satisfactorily improved.

In general, ferroelectric liquid crystal materials are prepared by adding an optically active compound called a chiral dopant to an achiral base liquid crystal composition showing a smectic C phase ($S_c$ phase). In many cases, phenylpyrimidine type liquid crystal compounds having advantageous viscosity properties are utilized as an achiral base. In actual use, however, properties of the resulting ferroelectric liquid crystal composition, such as viscosity and response time, greatly vary depending on the properties of optically active compounds added thereto.

Further, in order to obtain satisfactory orientation, ferroelectric liquid crystal compositions are demanded to have a smectic A phase ($S_A$ phase) and desirably a nematic phase in which orientation can be effected with relative ease in a higher temperature range.

As containing an optically active compound as mentioned above, a ferroelectric liquid crystal composition in its nematic phase shows a chiral nematic phase ($N^*$ phase) in which a helical structure is induced. If the helical pitch in the $N^*$ phase has temperature dependence, orientation would be difficult. Accordingly, the optically active compound to be added is required not only to provide a liquid crystal composition having the properties demanded as a ferroelectric liquid crystal but also to induce a chiral nematic phase whose helical pitch is less dependent on temperature.

An optically active compound is also used as a chiral dopant for nematic liquid crystal materials for use in nematic liquid crystal displays. In this case, an optically active compound is needed for preventing occurrence of so-called reverse domains in which liquid crystal molecules are twisted to an opposite direction and also for stably maintaining the angle of twist of molecules in the cell. Of the properties demanded for a chiral dopant for a nematic phase, a helical twisting power (HTP=1/concentration by weight×helical pitch) is the most important. A chiral dopant with a larger HTP value will be effective in a smaller amount, thus minimizing impairment of the characteristics inherent to host nematic liquid crystal mixtures.

Further, reduction of temperature dependence of a helical pitch in $N^*$ phase is an important factor for a chiral dopant to be added to nematic liquid crystals used in twisted nematic (TN) mode and super twisted nematic (STN) mode display elements. For example, if a chiral dopant shows high positive dependence on temperature (i.e., the pitch is broadened with an increase in temperature), it must be used in combination with a chiral dopant having an opposite tendency to offset the temperature dependence, which makes the chiral dopant mixing system complicated.

The chiral dopant currently used for nematic liquid crystals comprises a mixture of several kinds of optically active compounds for the purpose of controlling a helical pitch in the N* phase and reducing the temperature dependence of the helical pitch. Not a few of the known optically active compounds exhibit no liquid crystal properties and, when added to a nematic liquid crystal, cause a drop of the nematic-isotropic phase transition temperature.

SUMMARY OF THE INVENTION

An object of the present invention is to provide an optically active compound useful as a chiral dopant for ferroelectric liquid crystals which shows a chiral smectic phase by itself and provides a helical pitch with small temperature dependence in the chiral nematic phase.

Another object of the present invention is to provide an optically active compound useful as a chiral dopant for nematic liquid crystals which has a high HTP value, provides a helical pitch with small temperature dependence, and gives no adverse influence on the liquid crystal temperature range and other characteristics of the nematic liquid crystals.

A further object of the present invention is to provide an optically active compound which can be applied to various electro-optic devices using liquid crystals.

The present invention relates to an optically active compound represented by formula (I):

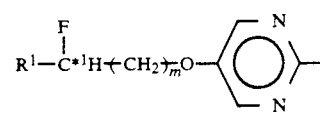

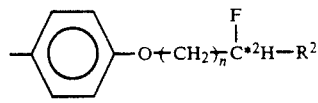

wherein $R^1$ represents an alkyl group having from 3 to 9 carbon atoms; $R^2$ represents an alkyl group having from 3 to 7 carbon atoms; m and n each represent 1 or 2 provided that they do not simultaneously represent 1; and $C^{*1}$ and $C^{*2}$ both represent an optically active carbon atom.

The present invention also relates to a liquid crystal composition containing at least one compound represented by formula (I).

DETAILED DESCRIPTION OF THE INVENTION

In formula (I), the alkyl group as represented by $R^1$ or $R^2$ may be straight or branched but is preferably straight. Specific examples of the alkyl group include straight chain alkyl groups, e.g., propyl, butyl, pentyl, hexyl, heptyl, octyl and nonyl groups; and branched alkyl groups having a methyl group as a branch, e.g.,

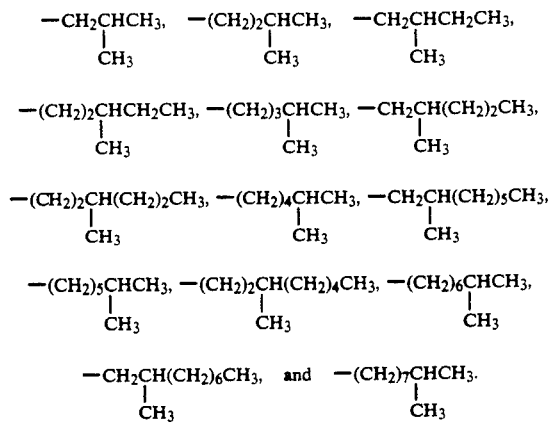

$R^1$ and $R^2$ may be the same or different, and may contain an optically active carbon atom.

Known optically active compounds relevant to the compounds of the present invention include fluorine-substituted compounds disclosed in JP-A-4-29954 (the term "JP-A" as used herein means an "unexamined published Japanese patent application") which are represented by formula (II):

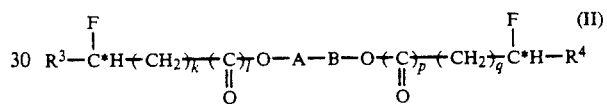

wherein $R^3$ and $R^4$ each represent an alkyl group having from 1 to 10 carbon atoms; A and B each represent

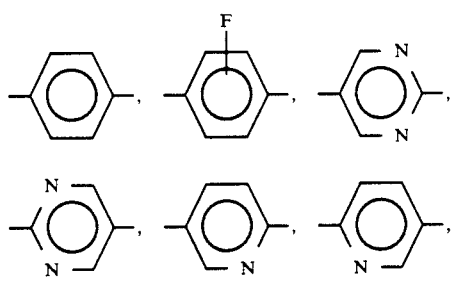

k, l, p, and q each represent 0 or 1; and * indicates an asymmetric carbon atom.

Various fluorine-substituted optically active compounds have been synthesized to date, and each of them is known to have a relatively large spontaneous polarization (Ps) and a low viscosity The compounds of formula (II) having a fluorine-substituted optically active carbon atom on each end side of the core seem to be the most excellent of all the known compounds in terms of Ps and viscosity. JP-A-4-29954 supra further has a mention that a compound represented by formula (III) exhibits ferroelectric liquid crystal phases.

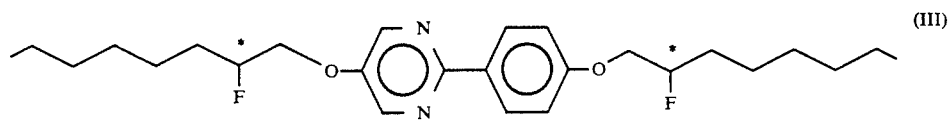

The compound of formula (III) is a compound of formula (II) wherein k and q each is 0 or 1.

The compounds of the present invention, in which either k or q is 2, are different from those disclosed in the above publication. In fact, the compounds specifically disclosed in the publication include no compound corresponding to the compounds of the present invention.

Also included in known optically active compounds are 2-fluoro-substituted optically active compounds represented by formula (IV) (refer to JP-A-63-22042, JP-A-1-207280, Nohira, et al. *Dai 13-kai Ekisho Toronkai Yokoshu* (*Preprint for the* 13*th Symposium of liquid crystals*), IZ02 (1987), etc.) or formula (V) (refer to JP-A-63-190842) and 3-fluoro-substituted compounds represented by formula (VI) (refer to JP-A-4-89483):

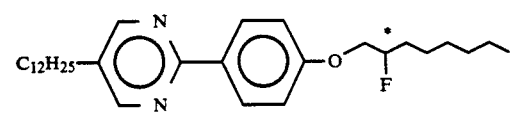

(IV)

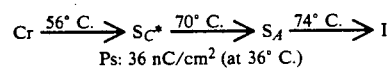

Ps: 36 nC/cm² (at 36° C.)

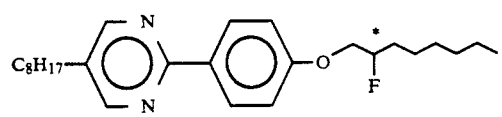

(V)

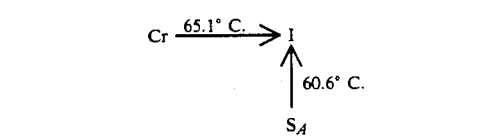

(VI)

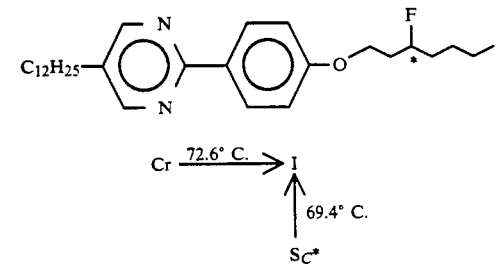

While many of these known compounds exhibit ferroelectric liquid crystal phases, they have disadvantages for serving as a chiral dopant, for example, large temperature dependence of the helical pitch in the chiral nematic phase (see JP-A-62-21963) or insufficient spontaneous polarization (see JP-A-4-89483). In addition, the HTP calculated from the helical pitch in the chiral nematic phase as disclosed is no more than about 2 for the 2-fluoro-substituted compounds (JP-A-62-21963 and JP-A-63-190842) and about 10 at the highest for the 3-fluoro-substituted compounds.

On comparing with these known compounds, the compounds according to the present invention are phenylpyrimidine type compounds having a 3-fluoro-substituted asymmetric carbon atom on one side of the phenylpyrimidine core and a 2- or 3-fluoro-substituted asymmetric carbon on the other side. While having a fluorine-substituted optically active carbon atom at a position remote from the core, the compounds of the present invention scarcely suffer from reduction of spontaneous polarization. By introducing a 3-fluorine-substituted optically active group and introducing a plurality of fluorine-substituted optically active groups, the compounds of the present invention exhibit a fast response and induces a chiral nematic phase whose helical pitch has very small temperature dependence.

In particular, the plural asymmetric carbon atoms of the compounds of the present invention perform an important function in connection with the direction, pitch, and temperature dependence of the helix appearing in the chiral nematic phase. For example, a compound of formula (I) wherein m and n are both 2 changes its direction of spontaneous polarization from negative to positive on replacement of (R)-asymmetric carbon on the benzene side with (S)-asymmetric carbon. Where the asymmetric carbon atom on the pyrimidine ring side is changed from (R) to (S), the direction of helix in the chiral nematic phase changes from left to right. Thus, the compounds of the present invention have such a great advantage that the direction of spontaneous polarization and the direction of the helix in the chiral nematic phase can be controlled separately by changing the steric configuration of each of the two asymmetric carbon atoms.

Further, a liquid crystal composition containing the optically active compound of the present invention, especially 3-fluorine-substituted compound shows a chiral nematic phase and undergoes no impairment of thermal stability of the nematic phase of the achiral base thereof, i.e., reduction of phase transition temperatures.

Furthermore, as demonstrated in Examples hereinafter described, the compounds of the present invention have a markedly higher HTP value with much lower dependence on temperature as compared with a commercially available chiral dopant for nematic liquid crystals "S-811" (HTP=about 10). Therefore, the compounds of the present invention are greatly useful as a chiral dopant for nematic liquid crystals.

In addition, the compounds of the present invention shows an Nhu * phase with very high thermal stability. Accordingly, they provide a liquid crystal composition showing an N* phase without adversely affecting the temperature range of an achiral base of the composition.

The known compounds disclosed in JP-A-4-29954 have a HTP value as low as from about 3 to 6 in the chiral nematic phase as proved in Comparative Example hereinafter described and are therefore of little practical use as a chiral dopant for nematic liquid crystals.

The optically active compounds of formula (I) are generally synthesized according to the following reaction schemes.

(A) Compounds Wherein n=m=2:

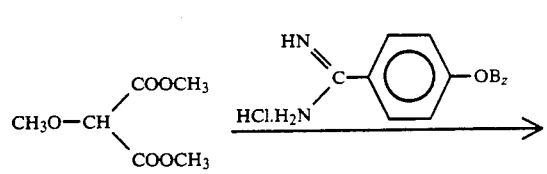

-continued
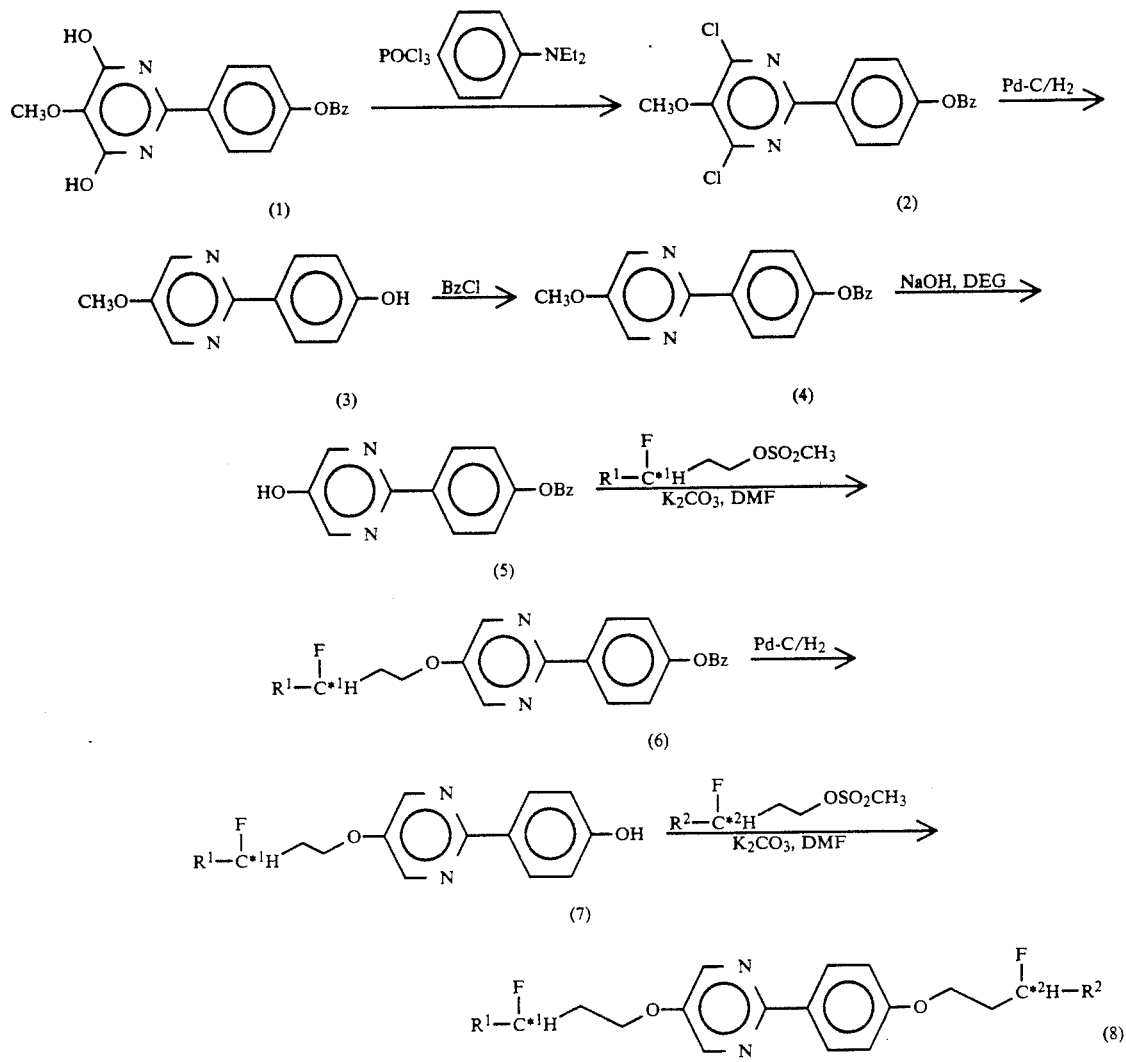
(B) Compounds Where m=1, n=2:
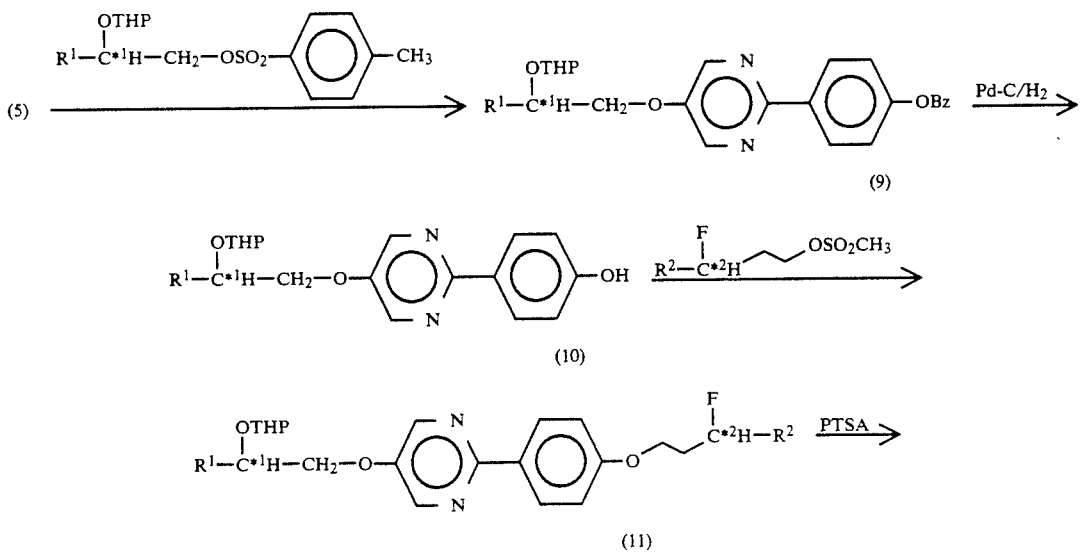

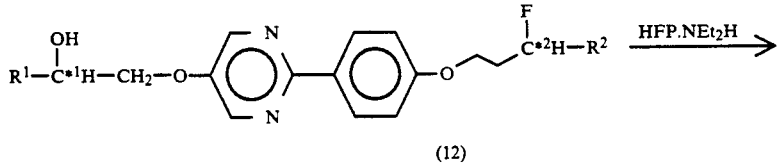

(12)

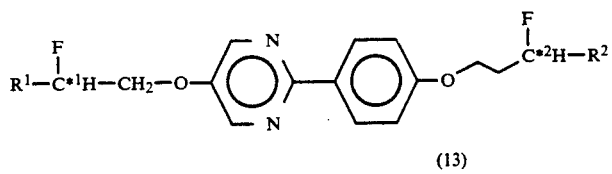

(13)

(C) Compounds Wherein m=2, n=1:

steric structure but causes no change in optical purity (see JP-A-4-89483).

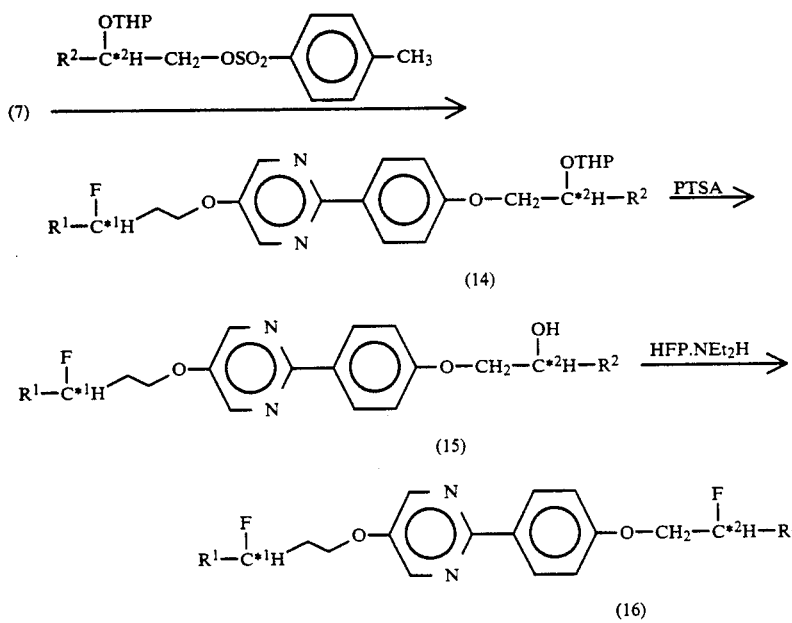

In process (A), dimethyl methoxymalonate and 4-benzyloxybenzamidine hydrochloride are reacted to obtain 4,6-dihydroxy-5-methoxy-2-(4-benzyloxyphenyl)pyrimidine (1), which is then chlorinated with phosphorus oxychloride to obtain a dichloro derivative (2). The compound (2) is debenzylated by hydrogenation using palladium-on-carbon to obtain 5-methoxy-2-(4-hydroxyphenyl)pyrimidine (3), which is again protected with a benzyl group [(3)→(4)], followed by demethylation [(4)→(5)]. Compound (5) is reacted with an optically active 3-fluoroalkyl mesylate to obtain compound (6). After removing the benzyl protective group by hydrogenation with palladium-on-carbon [(6)→(7)], compound (7) is reacted with an optically active 3-fluoroalkyl mesylate to obtain compound (8).

In process (B), compound (5) synthesized in process (A) is reacted with a 2-tetrahydropyranyloxyalkyl tosylate to obtain compound (9), which is then debenzylated by using palladium-on-carbon [(9)→(10)]Compound (10) is reacted with a 3-fluoroalkyl mesylate to obtain compound (11), followed by removal of the tetrahydropyranyl protective group [(11)→(12)]. Compound (12) is fluorinated with hexafluoropropenediethylamine to obtain compound (13). It has been confirmed that the fluorination of compound (12) induces inversion of the In process (C), compound (7) synthesized in process (A) is reacted with a 2-tetrahydropyranyloxyalkyl tosylate to synthesize compound (14). The tetrahydropyranyl group is removed by reacting with p-toluenesulfonic acid, and the resulting compound (15) is fluorinated in the same manner as in process (B) to obtain compound (16).

3-Fluoroalkanols, 2-tetrahydropyranyloxyalkanols and their methanesulfonic acid esters, and p-toluenesulfonic ester derivatives used in processes (A) to (C) can be synthesized in accordance with the processes disclosed in JP-A-4-89483.

Each of the compounds according to the present invention has four stereoisomers assigned to the two asymmetric carbon atoms thereof.

With respect to the limitation on carbon atom numbers of $R^1$ and $R^2$ in formula (I), if the carbon atom number of $R^1$ or $R^2$ is 2 or less, the temperature range of a $S_C^*$ phase will be narrowed. If $R^1$ contains more than 9 carbon atoms or if $R^2$ contains more than 7 carbon atoms, the viscosity will be increased to thereby retard the response to an applied voltage.

The present invention is now illustrated in greater detail with reference to Examples, but it should be understood that the present invention is not deemed to be limited thereto.

In the foregoing description and the following Examples, the cell used for measurements comprised a pair of glass substrates each having provided thereon a transparent indium-tin oxide electrode on which a polyvinyl alcohol was coated and rubbed to form an orientation film, assembled at a cell gap of about 2.5 μm. The rubbing direction on the two glass substrates was parallel. A spontaneous polarization (Ps) was obtained from a polarization inversion current with a triangular wave of ±10 V applied. A tilt angle was obtained from the extinction position under a crossed Nicol with a square wave of ±20 V applied. A response time was obtained from the speed of change of transmitted light under the same conditions as in the measurement of the tilt angle. The helical pitch in the N* phase was measured by use of a Cano's wedge cell.

Abbreviations hereinafter used have the following meanings:
I: Isotropic liquid phase
N*: Chiral nematic phase
$S_A$: Smectic A phase
$S_C^*$: Chiral smectic C phase
Cr: Crystal phase
Ps: Spontaneous polarization In Examples and Comparative Example, all the percents are by weight unless otherwise indicated.

EXAMPLE 1

Synthesis of
5-[3-(R)-Fluoroheptyloxy]-2-[4-{3-(R)-fluorohexyloxy} phenyl]pyrimidine

Step 1: Synthesis of
4,6-Dihydroxy-5-methoxy-2-(4-benzyloxyphenyl)-pyrimidine A mixture of 85 g of 4-benzyloxybenzamidine hydrochloride, 78.6 g of dimethyl methoxymalonate, 1700 ml of ethanol, and 187 g of sodium methylate (28% methanol solution) was heated at 80° C. for 4 hours with stirring. After cooling, 1000 ml of acetic acid was slowly added to the reaction mixture, whereupon a yellow crystal precipitated. The precipitated crystals were collected by filtration, washed twice with water until the washing became neutral, and dried at 80° C. for 3 hours in high vacuo to obtain 64.2 g (percent yield: 60.7% ) of 4,6-dihydroxy-5-methoxy-2-(4-benzyloxyphenyl)pyrimidine.

Melting point: 251°–252.4° C.

Step 2: Synthesis of
4,6-Dichloro-5-methoxy-2-(4-benzyloxyphenyl)pyrimidine.

In a reactor were charged 30.0 g of 4,6-dihydroxy-5-methoxy-2-(4-benzyloxyphenyl)pyrimidine and 35.0 g of N,N-diethylaniline in a nitrogen atmosphere, and 85.0 g of phosphorus oxychloride was added thereto, followed by heating at 105° C. for 4 hours with stirring. The reaction mixture was poured into 100 ml of a 1% sodium carbonate aqueous solution. The precipitated crystals were filtered, washed with water, and dried to give 21.0 g (percent yield: 53.0%) of 4,6-dichloro-5-methoxy-2-(4-benzyloxyphenyl)pyrimidine.

Step 3: Synthesis of
5-Methoxy-2-(4-hydroxyphenyl)pyrimidine

Hydrogen gas was blown into a mixture of 21 g of 4,6-dichloro-5-methoxy-2-(4-benzyloxyphenyl)pyrimidine, 18.1 g of triethylamine, 3.15 g of 10% palladium-on-carbon, 210 ml of ethanol, and 11 ml of water, followed by stirring at 40° C. for 6 hours. The catalyst was removed by filtration, and the filtrate was poured into 300 ml of water and extracted with ethyl acetate. The extract was dried over anhydrous sodium sulfate and distilled to remove ethyl acetate to afford 8.93 g (percent yield: 90.9%) of 5-methoxy-2-(4-hydroxyphenyl)-pyrimidine.

Step 4: Synthesis of
5-Methoxy-2-(4-benzyloxyphenyl)-pyrimidine

A mixture of 9.0 g of 5-methoxy-2-(4-hydroxyphenyl)pyrimidine, 8.45 g of benzyl chloride, 270 ml of dimethylformamide (DMF), and 12.3 g of potassium carbonate was stirred at 80° C. for 4 hours. The reaction mixture was diluted with water and extracted with ethyl acetate. The extract was washed with water and distilled to remove ethyl acetate to obtain 8.42 g (percent yield: 64.2%) of 5-methoxy-2-(4-benzyloxyphenyl)pyrimidine.

Step 5: Synthesis of
5-Hydroxy-2-(4-benzyloxyphenyl)-pyrimidine

A mixture of 8.42 g of 5-methoxy-2-(4-benzyloxyphenyl)pyrimidine, 6.9 g of sodium hydroxide, and 84 ml of diethylene glycol was heated at 190° to 200° C. for 2 hours. After cooling, the reaction mixture was poured into 300 ml of water, neutralized with a 1% hydrochloric acid aqueous solution, and extracted with ethyl acetate. Distillation of the extract to remove ethyl acetate gave 7.3 g (26.2 mmol; percent yield: 91.8%) of 5-hydroxy-2-(4-benzyloxyphenyl)pyrimidine.

Melting point: 183.3° C.
MS (m/e): 278(M+), 187
NMR (δ, ppm): 5.13 (2H, s), 7.07 (2H, d, J=8.8Hz), 7.33–7.46 (5H, m), 8.28 (2H, d, J=8.6Hz), 8.48 (2H, s)

Step 6: Synthesis of
5-[3-(R)-Fluoroheptyloxy]-2-(4-benzyloxyphenyl)-pyrimidine A mixture of 1.12 g of 5-hydroxy-2-(4-benzyloxyphenyl)pyrimidine, 1.30 g of 3-(R)-fluoroheptyl methanesulfonate, 1.2 g of potassium carbonate, and 50 ml of DMF was stirred at 80° C. for 4 hours. After cooling, the reaction mixture was diluted with water and extracted with ethyl acetate. The extract was washed with water and distilled to remove the solvent to obtain a residue weighing 2.12 g. Recrystallization of the residue from ethanol furnished 1.41 g (percent yield: 87.7%) of 5-[3-(R)-fluoroheptyloxy]-2-(4-benzyloxyphenyl)-pyrimidine.

Step 7: Synthesis of
5-[3-(R)-Fluoroheptyloxy]-2-(4-hydroxyphenyl)pyrimidine A mixture of 1.41 g of 5-[3-(R)-fluoroheptyloxy]-2-(4-benzyloxyphenyl)pyrimidine, 0.22 g of 10palladium-on-carbon, 14 ml of methanol, and 14 ml of tetrahydrofuran (THF) was kept at 30° C., and hydrogen gas was blown thereinto over 6 hours with stirring. The catalyst was removed by filtration, and the solvent was removed by distillation to obtain 1.11 g of 5-[3-(R)-fluoroheptyloxy]-2-(4-hydroxyphenyl)pyrimidine.

$[\alpha]_D^{20}$: −14.32°

Step 8: Synthesis of
5-[3-(R)-Fluoroheptyloxy]-2-[4-{3-(R)-fluorohexyloxy}phenyl]pyrimidine A mixture of 0.86 g of 5-[3-(R)-fluoroheptyloxy]-2-(4-hydroxyphenyl)pyrimidine, 0.56 g of (R)-3-fluorohexyl methanesulfonate, 1.2 g of potassium carbonate, and 30 ml of DMF was stirred at 80° C. for 4 hours. The reaction mixture was cooled, poured into 50 ml of water, and extracted with ethyl acetate. The extract was washed with water and dried over anhydrous sodium sulfate. The solvent was removed by distillation to obtain a residue weighing 2.03 g, which was purified by column chromatography on silica gel and then by high performance liquid chromatography (HPLC) to obtain 0.40 g (percent yield: 34.82%) of 5-[3-(R)]-fluoroheptyloxy]-2-[4-{3-(R)-fluorohexyloxy}phenyl]pyrimidne.

$[\alpha]_D^{20}$: −23.26°

MS (m/e): 407(M+) NMR (δ, ppm): 0.93 (3H, t, J=7.2Hz), 0.96 (3H, t, J=7.2Hz), 1.35–1.80 (10H, m), 2.06 (2H, m), 2.11 (2H, m), 4.13–4.26 (4H, m), 4.76 (2H, dm, J=50.3Hz), 6.98 (2H, d, J=9.0Hz), 8.29 (2H, d, J=9.0Hz), 8.42 (2H, s)

EXAMPLE 2

Synthesis of
5-[3-(R)-Fluorooctyloxy]-2-[4-(3-(R)-fluorohexyloxy)-phenyl]pyrimidine The titled compound was synthesized in the same manner as in Example except for replacing 3-(R)-fluoroheptyl methanesulfonate with 3-(R)-fluorooctyl methanesulfonate. $[\alpha]_D^{20}$: −21.9°

MS (m/e): 420(M+)

NMR (δ, ppm): 0.91 (3H, t, J=7.0Hz), 0.97 (3H, t, J=7.2Hz), 1.31–1.71 (12H, m), 2.05 (2H, m), 2.11 (2H, m), 4.14–4.27 (4H, m), 4.77 (2H, dm, J=48.5Hz), 6.98 (2H, d, J=8.9Hz), 8.29 (2H, d, J=8.9Hz), 8.43 (2H, s)

EXAMPLE 3

Synthesis of
5-[3-(R)-Fluorononyloxy]-2-[4-{3-(R)-fluorohexyloxy}phenyl]pyrimidine The titled compound was synthesized in the same manner as in Example 1, except for replacing 3-(R)-fluoroheptyl methanesulfonate with 3-(R)-fluorononyl methanesulfonate.

$[\alpha]_D^{20}$: −19.85°

MS (m/e): 434(M+)

NMR (δ, ppm): 0.90 (3H, t, J=6.9Hz), 0.97 (3H, t, J=7.3Hz), 1.28–1.80 (14H, m), 2.00–2.17 (4H, m), 4.12–4.29 (4H, m), 4.77 (2H, dm, J=48.2Hz), 6.98 (2H, d, J=8.9Hz), 8.29 (2H, d, J=8.9Hz), 8.43 (2H, s)

EXAMPLE 4

Synthesis of
5-[3-(R)-Fluorodecyloxy]-2-[4-{3-(R)-fluorohexyloxy}phenyl]pyrimidine The titled compound was synthesized in the same manner as in Example 1, except for replacing 3-(R)-fluoroheptyl methanesulfonate with 3-(R)-fluorodecyl methanesulfonate.

$[\alpha]_D^{20}$: −19.26°

MS (m/e): 448(M+)

NMR (δ, ppm): 0.89 (3H, t, J=6.9Hz), 0.97 (3H, t, J=7.3Hz), 1.25–1.80 (16H, m), 2.01–2.18 (4H, m), 4.12–4.29 (4H, m), 4.76 (2H, dm, J=47.9Hz), 6.98 (2H, d, J=9.0Hz), 8.29 (2H, d, J=8.9Hz), 8.43 (2H, s)

EXAMPLE 5

Synthesis of
5-[3-(R)-Fluorododecyloxy]-2-[4]-{3-(R)-fluorohexyloxy}phenyl]pyrimidine The titled compound was synthesized in the same manner as in Example 1, except for replacing 3-(R)-fluoroheptyl methanesulfonate with 3-(R)-fluorododecyl methanesulfonate. $[\alpha]_D^{20}$: −18.17°

MS (m/e): 476(M+)

NMR (δ, ppm): 0.88 (3H, t, J=6.9Hz), 0.97 (3H, t, J=7.3Hz), 1.23–1.79 (20H, m), 2.00–2.18 (4H, m), 4.12–4.28 (4H, m), 4.77 (2H, dm, J=47.9Hz), 6.98 (2H, d, J=9.0Hz), 8.29 (2H, d, J=8.9Hz), 8.44 (2H, s)

EXAMPLE 6

Synthesis of
5-[3-(S)-Fluorooctyloxy]-2-[4-{3-(S)-fluoroheptyloxy}phenyl]pyrimidine The titled compound was synthesized in the same manner as in Example 1, except for replacing 3-(R)-fluoroheptyl methanesulfonate and 3-(R)-fluorohexyl methanesulfonate with 3-(S)-fluorooctyl methanesulfonate and 3-(S)-fluoroheptyl methanesulfonate, respectively.

$[\alpha]_D^{20}$: +21.6°

MS (m/e): 434(M+)

NMR (δ, ppm): 0.88–0.96 (6H, m), 1.29–1.80 (14H, m), 2.03–2.17 (4H, m), 4.12–4.29 (4H, m), 4.77 (2H, dm, J=49.6Hz), 6.98 (2H, d, J=9.0Hz), 8.29 (2H, d, J=8.9Hz), 8.44 (2H, s)

EXAMPLE 7

Synthesis of
5-[3-(R)-Fluorooctyloxy]-2-[4-{3-(R)-fluoroheptyloxy}phenyl]pyrimidine The titled compound was synthesized in the same manner as in Example 2, except for replacing 3-(R)-fluorohexyl methanesulfonate with 3-(R)-fluoroheptyl methanesulfonate.

$[\alpha]_D^{20}$: −20.8°

MS (m/e): 434(M+)

NMR (δ, ppm): 0.91 (3H, t, J=6.9Hz), 0.93 (3H, t, J=7.0Hz), 1.29–1.80 (14H, m), 2.00–2.17 (4H, m), 4.11–4.28 (4H, m), 4.77 (2H, dm, J=49.8Hz), 6.98 (2H, d, J=8.9Hz), 8.29 (2H, d, J=8.8Hz), 8.43 (2H, s)

EXAMPLE 8

Synthesis of
5-[3-(R)-Fluorohexyloxy]-2-[4-{3-(R)-fluorohexyloxy}phenyl]pyrimidine The titled compound was synthesized in the same manner as in Example 1, except for replacing 3-(R)-fluoroheptyl methanesulfonate with 3-(R)-fluorohexyl methanesulfonate.

$[\alpha]_D^{20}$: −24.01°

MS (m/e): 392(M+)

NMR (δ, ppm): 0.97 (3H, t, J=7.2Hz), 0.98 (3H, t, J=7 2Hz), 1.40–1.80 (8H, m), 2.06 (2H, m), 2.12 (2H, m), 4.14–4.25 (4H, m), 4.77 (2H, dm, J=50.0Hz), 6.98 (2H, d, J=9.0Hz), 8.29 (2H, d, J=9.0Hz), 8.43 (2H, s)

EXAMPLE 9

Synthesis of 5-[3-(S)-Fluorononyloxy]-2-[4-{3-(S)-fluoroheptyloxy}phenyl]pyrimidine The titled compound was synthesized in the same manner as in Example 6, except for replacing 3-(S)-fluorooctyl methanesulfonate with 3-(S)-fluorononyl methanesulfonate. $[\alpha]_D^{20}$: +20.1°

MS (m/e): 448(M+)

NMR δ, ppm): 0.90 (3H, t, J=7.0Hz), 0.93 (3H, t, J=7.0Hz), 1.28–1.78 (16H, m), 2.05 (2H, m), 2.12 (2H, m), 4.12–4.3 (4H, m), 4.76 (2H, dm, J=49.4Hz), 6.98 (2H, d, J=9.0Hz), 8.28 (2H, d, J=9.0Hz), 8.43 (2H, s)

EXAMPLE 10

Synthesis of 5-[3-(R)-Fluorooctyloxy]-2-[4-{3-(R)-fluorodecyloxy}phenyl]pyrimidine The titled compound was synthesized in the same manner as in Example 2, except for replacing 3-(R)-fluorohexyl methanesulfonate with 3-(R)-fluorodecyl methanesulfonate.

$[\alpha]_D^{20}$: −17.3°

MS (m/e): 476(M+)

NMR (δ, ppm): 0.89 (3H, t, J=6.9Hz), 0.91 (3H, t, J=7.1Hz), 1.25–1.80 (20H, m), 2.02–2.18 (4H, m), 4.12–4.30 (4H, m), 4.76 (2H, dm, J=48.8Hz), 6.98 (2H, d, J=9.0Hz), 8.29 (2H, d, J=8.9Hz), 8.44 (2H, s)

EXAMPLE 11

Synthesis of 5-[2-(S)-Fluoroheptyloxy]-2-[4-{3-(R)-fluoroheptyloxy}phenyl]pyrimidine Step 1: Synthesis of 5-[2-(R)-Tetrahydropyranyloxyheptyloxy]-2-(4-benzyloxyphenyl)pyrimidine:

In a 500 ml four-necked flask were charged 12.2 g (43.7 mmol) of 5-hydroxy-2-(4-benzyloxyphenyl)-pyrimidine, 24 g (65.5 mmol) of (R)-2-tetrahydropyranyloxyheptyl tosylate, 12 g of potassium carbonate, and 183 ml of DMF, and the mixture was stirred at 80° C. for 5 hours. After cooling, the reaction mixture was poured into 500 ml of ice-water and extracted with ethyl acetate. The extract was washed with water, and the solvent was removed by distillation under reduced pressure to obtain 28.6 g of a crude product, which was purified by silica gel column chromatography to obtain 25.3 g of the titled compound.

$[\alpha]_D^{26}$: +18.9°

Step 2: Synthesis of 5-[2-(R)-Tetrahydropyranyloxyheptyloxy]-2-(4-hydroxyphenyl)pyrimidine.

In a 2 l four-necked flask were charged 25.3 g (51.2 mmol) of the compound obtained in step 1, 506 ml of THF, and 506 ml of methanol. After purging the flask with nitrogen, 5 g of 10% palladium-on-carbon was added thereto to conduct hydrogenation at 30° to 35° C. under atmospheric pressure for 2 hours. After completion of the reaction, the catalyst was removed by filtration in a nitrogen stream, and the solvent was recovered to afford 20.18 g of the titled compound.

$[\alpha]_D^{26}$: +19.3°

Step 3: Synthesis of 5-[2-(R)-Tetrahydropyranyl-oxyheptyloxy]-2-[4-{3-(R)-fluoroheptyl-oxy}phenyl]pyrimidine In a reaction flask were charged 5 g of the compound obtained in step 2, 4.1 g of 3-(R)-fluoroheptyl mesylate, 3.58 g of potassium carbonate, and 100 ml of DMF in a nitrogen stream, followed by allowing the mixture to react at 80° C. for 12 hours. After cooling, the reaction mixture was poured into water and extracted with ethyl acetate. The solvent was removed from the extract to give 8.1 g of a crude product. Purification by silica gel column chromatography yielded 6.96 g of the titled compound.

Step 4: Synthesis of 5-[2-(R)-Hydroxyheptyloxy]-2-[4-{3-(R)-fluoroheptyloxy}phenyl]pyrimidine In a 1 l four-necked flask were charged 6.96 g of the compound obtained in step 3 and 750 ml of methanol, and 354 ml of a 0.4% methanol solution of p-toluenesulfonic acid was added thereto dropwise at 5° C. over a period of 1 hour. The reaction mixture was allowed to further react at 20° C. for 2 hours. The reaction mixture was neutralized with a sodium bicarbonate aqueous solution, and methanol was removed by distillation. The residue was extracted with ethyl acetate, and the extract was washed with water and concentrated to obtain 5.5 g of a crude product. Purification of the crude product by silica gel column chromatography gave 4.9 g of the titled compound.

$[\alpha]_D^{20}$: −19.1°

Step 5: Synthesis of 5-[2-(S)-Fluoroheptyloxy]-2-[4-{3-(R)-fluoroheptyloxy}phenyl]pyrimidine In a 300 ml four-necked flask were charged 4.9 g of the compound obtained in step 4 and 125 ml of methylene chloride, and a solution of 3.2 g of hexafluoropropenediethylamine in 32 ml of methylene chloride was added thereto dropwise at 30° C. over 1 hour, followed by stirring at the same temperature for 1 hour. The reaction mixture was poured into water for washing, followed by concentration of methylene chloride solution to obtain 4.9 g of a crude product. The crude product was purified by recrystallization from ethanol and then by HPLC to afford 0.84 g of the titled compound.

$[\alpha]_D^{20}$: −7.76°

MS (m/e): 420 (M+)

NMR (δ, ppm): 0.90–0.94 (6H, m), 1.30–1.88 (14H, m), 2.00–2.13 (2H, m), 4.12–4.23 (4H, m), 4.77 (1H, dm, J=49.4Hz), 4.86 (1H, dm, J=48.4Hz), 7.20 (2H, d, J=8.9Hz), 8.29 (2H, d, J=8.9Hz), 8.46 (2H, s)

EXAMPLE 12

Synthesis of 5-[3-(S)-Fluoroheptyloxy]-2-[4-{2-(R)-fluoroheptyloxy}phenyl]pyrimidine Step 1: Synthesis of 5-[3-(S)-Fluoroheptyloxy]-2-[4-{2-(S)-tetrahydropyranyloxyheptyloxy}phenyl]-pyrimidine In a reaction flask were charged 3.5 g of 5-[3-(S)-fluoroheptyloxy]-2-(4-hydroxyphenyl)pyrimidine synthesized in the same manner as in steps 1 to 7 of Example 1, 3.17 g of potassium carbonate, 70 ml of DMF, and 6.4 g of 2-(S)-tetrahydropyranyloxyheptyl tosylate in a nitrogen stream, and the mixture was allowed to react at 80° C. for one day. After cooling, water was added thereto, the reaction mixture was extracted with toluene, and the solvent was removed from the extract to obtain 7.6 g of a crude product. Purification by silica gel column chromatography gave 6.4 g of the titled compound.

Step 2: Synthesis of
5-[3-(S)-Fluoroheptyloxy]-2-[4-{2-(S)-hydroxyheptyloxy}phenyl]pyrimidine In a reaction flask were charged 6.4 g of the compound obtained in step 1 and 485 ml of methanol, followed by cooling to 5° C. A solution of 0.805 g of p-toluenesulfonic acid (monohydrate) in 201.5 ml of methanol was added thereto dropwise at that temperature over 1 hour. After the addition, the reaction temperature was elevated to 20° C., and the mixture was stirred at that temperature until the reaction completed while monitoring the unreacted substance by HPLC. After completion of the reaction, the reaction mixture was neutralized with a sodium hydrogencarbonate aqueous solution, and methanol was removed by distillation under reduced pressure to obtain 7.0 g of a crude product. Purification by silica gel column chromatography furnished 2.87 g of the titled compound.
$[\alpha]_D^{20}$: +24.8°

Step 3: Synthesis of
5-[3-(S)-Fluoroheptyloxy]-2-[4-{2-(R)-fluoroheptyloxy}phenyl]pyrimidine In a reaction flask were charged 2.5 g of the compound obtained in step 2 and 85.5 ml of methylene chloride, and the mixture was heated to 30° C. A solution of 1.68 g of hexafluoropropenediethylamine in 10 ml of methylene chloride was added thereto dropwise at that temperature over 30 minutes. After the addition, the reaction was further continued for an additional one hour. The reaction mixture was washed in ice-water and neutralized with a sodium hydrogencarbonate aqueous solution, and the solvent was removed by distillation under reduced pressure to obtain 4.0 g of a crude product. The crude product was purified by silica gel column chromatography and then by HPLC. Recrystallization from ethanol yielded 0.81 g of the titled compound.
$[\alpha]_D^{20}$: +10.6°
MS (m/e): 420(M+)
NMR (δ, ppm): 0.89–0.95 (6H, m), 1.3–1.87 (14H, m), 2.05–2.18 (2H, m), 4.07–4.30 (4H, m), 4.76 (1H, dm, J=49.6Hz), 4.86 (1H, dm, J=50.2Hz), 7.20 (2H, d, J=8.9Hz), 8.29 (2H, d, J=8.9Hz), 8.46 (2H, s)

Phase transition temperatures of the compounds synthesized in Examples 1 to 12 are shown in Table 1 below. Under the heads of $C^{*1}$ and $C^{*2}$ are shown the absolute configuration of the respective asymmetric carbon atom. $S_3$ means an unidentified higher-order smectic phase.

TABLE 1

| Example No. | $R^1$ | $C^{*1}$ | m | n | $C^{*2}$ | $R^2$ | Cr | $S_3$ | $S_C^*$ | N | I |
|---|---|---|---|---|---|---|---|---|---|---|---|
| 1 | $C_4H_9$ | R | 2 | 2 | R | $C_3H_7$ | ·80.6 | — | (·73.8) | ·83.8 | · |
| 2 | $C_5H_{11}$ | R | 2 | 2 | R | $C_3H_7$ | ·66.9 | — | ·81.7 | ·87.6 | · |
| 3 | $C_6H_{13}$ | R | 2 | 2 | R | $C_3H_7$ | ·69.5 | — | ·88.2 | ·88.5 | · |
| 4 | $C_7H_{15}$ | R | 2 | 2 | R | $C_3H_7$ | ·69.3 | — | ·93.4 | — | · |
| 5 | $C_9H_{19}$ | R | 2 | 2 | R | $C_3H_7$ | ·70.9 | — | ·97.6 | — | · |
| 6 | $C_5H_{11}$ | S | 2 | 2 | S | $C_4H_9$ | ·70.3 | — | ·85.5 | ·87.8 | · |
| 7 | $C_5H_{11}$ | R | 2 | 2 | R | $C_4H_9$ | ·67.8 | — | ·85.2 | ·87.6 | · |
| 8 | $C_3H_7$ | R | 2 | 2 | R | $C_3H_7$ | ·81.0 | — | — | ·86.2 | · |
| 9 | $C_6H_{13}$ | S | 2 | 2 | S | $C_4H_9$ | ·75.3 | — | ·89.3 | — | · |
| 10 | $C_5H_{11}$ | R | 2 | 2 | R | $C_7H_{15}$ | ·69.5 | — | ·90.7 | ·91.3 | · |
| 11 | $C_5H_{11}$ | S | 1 | 2 | R | $C_4H_9$ | ·79.3 | (·77.6) | — | ·82.4 | · |
| 12 | $C_4H_9$ | S | 2 | 1 | R | $C_5H_{11}$ | ·67.3 | ·81.9 | ·83.9 | ·84.9 | · |

EXAMPLE 13

Of the compounds of formula (I), those showing only a chiral nematic phase can be added to a smectic C liquid crystal composition containing no chiral component to provide a ferroelectric liquid crystal composition.

A smectic C liquid crystal composition containing no optically active compound (hereinafter designated liquid crystal composition A) and its phase transition temperatures are shown below.

Liquid Crystal Composition A:

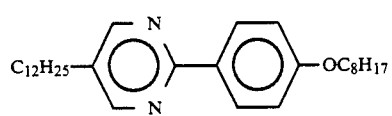
16.57 mol %

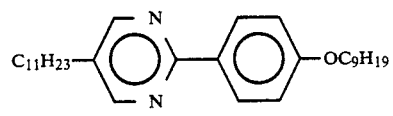
16.71 mol %

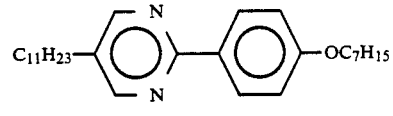
16.62 mol %

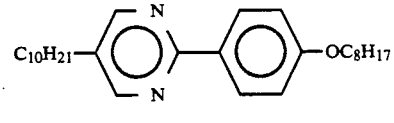
16.69 mol %

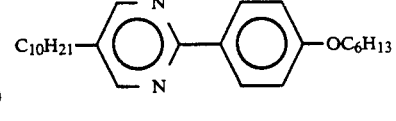
16.60 mol %

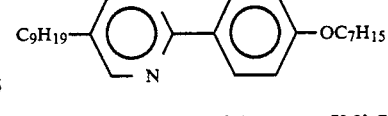
16.79 mol %

$Cr \xrightarrow{21.7° \text{ C.}} S_C \xrightarrow{63.8° \text{ C.}} S_A \xrightarrow{73.9° \text{ C.}} I$ The compound synthesized in Example 8 was added to liquid crystal composition A in a proportion of 23.97 mol%. There was obtained a ferroelectric liquid crystal composition exhibiting a nematic phase and a fast response.

Ferroelectric Liquid Crystal Composition

Liquid crystal composition A 76.03 mol %
                              23.97 mol %

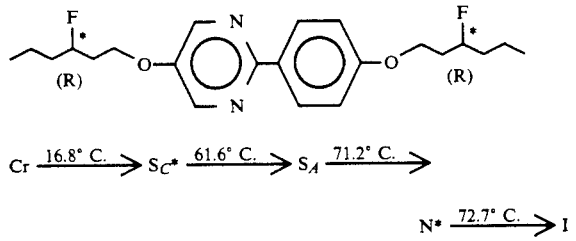

$$Cr \xrightarrow{16.8° C.} S_{C^*} \xrightarrow{61.6° C.} S_A \xrightarrow{71.2° C.}$$

$$N^* \xrightarrow{72.7° C.} I$$

Properties of the resulting ferroelectric liquid crystal composition are shown in Table 2 below.

TABLE 2

| Measuring Temperature (°C.) | Response Time (μsec) | Spontaneous Polarization (Ps) (nC/cm²) | Tilt Angle (°) |
|---|---|---|---|
| 51.6 | 17.0 | 14.3 | 18.5 |
| 41.6 | 26.2 | 18.4 | 20.0 |
| 31.6 | 40.4 | 23.2 | 22.0 |

EXAMPLE 14

In order to examine the functions of the compounds of the present invention as a chiral dopant for a nematic liquid crystal material, each of the compounds shown in Table 3 below was added to a commercially available nematic liquid crystal composition ("ZLI-2582" produced by Merck Co.) in a concentration of 1% or 5%.

The direction and pitch of the helix appearing in the N* phase at 60° C., the HTP value calculated from the helical pitch, and the temperature dependence of the helical pitch were determined. The temperature dependence of the helical pitch was obtained from $(P_{MAX} - P_{MIN})/(P_{MIN} \times |T_{MAX} - T_{MIN}|) \times 100$, wherein $P_{MAX}$ and $P_{MIN}$ represent a maximum pitch and a minimum pitch of the helix appearing in the measuring temperature range (30° to 90° C.), respectively; and $T_{MAX}$ and $T_{MIN}$ represent a temperature at which the maximum pitch and the minimum pitch appears, respectively. The closer to zero the value, the lower the temperature dependence. The results obtained are shown in Table 3.

TABLE 3

| Example No. of Compound | Concentration (%) | Direction of Helix in N* Phase | Helical Pitch in N* Phase (μm) | HTP (μm⁻¹) | Temperature Dependence of Helical Pitch |
|---|---|---|---|---|---|
| 1 | 5 | L | 1.7 | 11.8 | 0.09 |
| 2 | 5 | L | 1.6 | 12.5 | 0.32 |
| 3 | 5 | L | 0.84 | 23.8 | 0.31 |
| 4 | 5 | L | 0.78 | 25.6 | 0.40 |
| 5 | 5 | L | 0.8 | 25 | 0.33 |
| 6 | 1 | R | 3.8 | 26.1 | 0.13 |
| 7 | 5 | L | 1.6 | 12.5 | 0.09 |
| 8 | 5 | L | 0.82 | 24.4 | 0.13 |
| 9 | 5 | R | 1.7 | 11.8 | 0.69 |
| 10 | 1 | L | 3.6 | 27.8 | 0.39 |
| 11 | 5 | L | 1.3 | 15.4 | 0.14 |
| 12 | 5 | R | 1.3 | 15.4 | 0.04 |

From the results in Table 3, it is seen that many of the compounds according to the present invention, when added to a nematic liquid crystal material as a chiral dopant, induces a helical structure having small temperature dependence, mostly less than 0.4. Further, the pitch of the helical structure can adequately be adjusted by selecting the steric configuration of the optically active carbon atoms of the compound.

More specifically, where the positions of the asymmetric carbon atoms on both sides of the core are the same, compounds in which these asymmetric carbon atoms have the same absolute configuration have a high HTP value and are effective as a chiral dopant for a nematic phase.

COMPARATIVE EXAMPLE 1

A compound represented by formula shown below which is disclosed in JP-A-4-29954 was synthesized and added to the nematic liquid crystal composition ZLI-2582 in a proportion of 5.017%.

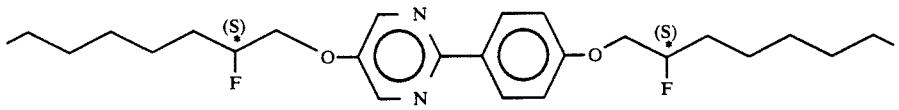

The phase transition temperatures of this compound were as follows.

$$Cr \xrightarrow{77.5° C.} S_3 \xrightarrow{89.6° C.} S_{C^*} \xrightarrow{90.5° C.} S_A \xrightarrow{95.1° C.} I$$

The helical pitch and HTP of the resulting liquid crystal composition at a varied temperature were as follows.

| Measuring Temperature (°C.) | Helical Pitch (μm) | HTP |
| --- | --- | --- |
| 30 | 6.14 | 3.2 |
| 40 | 4.89 | 4.1 |
| 50 | 4.09 | 4.9 |
| 60 | 3.64 | 5.5 |

EXAMPLE 15

The compound synthesized in Example 6 was added to the nematic liquid crystal composition ZLI-2582 in a proportion of 1.005%. The helical pitch and HTP of the resulting composition in its chiral nematic phase at a varied temperature are shown below.

| Measuring Temperature (°C.) | Helical Pitch (μm) | HTP |
| --- | --- | --- |
| 30 | 3.50 | 28.4 |
| 40 | 3.64 | 27.4 |
| 50 | 3.73 | 26.7 |
| 60 | 3.82 | 26.1 |

On comparing the results of Comparative Example 1 and Example 15, it is seen that the compound disclosed in JP-A-4-29954 suffers from considerable changes of the helical pitch with a change in temperature between 30° C. and 60° C., whereas the compound of Example 6 shows a change of the helical pitch by less than 10% in that temperature range, showing markedly reduced temperature dependence. In addition, the compound of Example 6 has a very high HTP value, proving remarkably excellent as a chiral dopant for a nematic phase.

As described and demonstrated above, many of the optically active compounds according to the present invention exhibit a chiral smectic phase, large spontaneous polarization, and a low viscosity, and induces a helical structure in the chiral nematic phase with small temperature dependence of the helical pitch and are therefore very useful as a chiral dopant for a ferroelectric liquid crystal material. Further, when added to a nematic liquid crystal as a chiral dopant, the compounds of the present invention have so high HTP value that a helical structure can be induced with a greatly reduced amount without adversely affecting the characteristics of the achiral nematic base.

Accordingly, the compounds of the present invention are extremely useful as a chiral dopant for ferroelectric liquid crystals or nematic liquid crystals and applicable to various electro-optic elements, etc. using liquid crystals.

While the invention has been described in detail and with reference to specific examples thereof, it will be apparent to one skilled in the art that various changes and modifications can be made therein without departing from the spirit and scope thereof.

What is claimed is:

1. An optically active compound represented by formula (I):

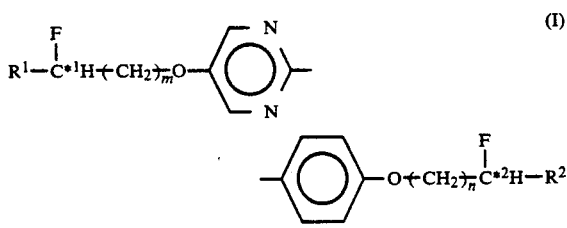

wherein $R^1$ represents an alkyl group having from 3 to 9 carbon atoms; $R^2$ represents an alkyl group having from 3 to 7 carbon atoms; m and n each represent 1 or 2 provided that they do not simultaneously represent 1; and $C^{*1}$ and $C^{*2}$ both represent an optically active carbon atom.

2. A liquid crystal composition containing at least one compound represented by formula (I):

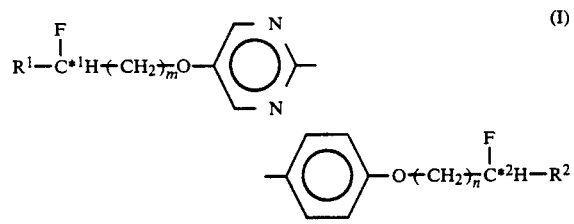

wherein $R^1$ represents an alkyl group having from 3 to 9 carbon atoms; $R^2$ represents an alkyl group having from 3 to 7 carbon atoms; m and n each represent 1 or 2 provided that they do not simultaneously represent 1; and $C^{*1}$ and $C^{*2}$ both represent an optically active carbon atom.

* * * * *